United States Patent [19]

Endo et al.

[11] Patent Number: 5,185,255
[45] Date of Patent: Feb. 9, 1993

[54] CELL CULTURE METHOD

[75] Inventors: Isao Endo, Kokubunji; Teruyuki Nagamune, Kamifukuoka; Minoru Nishimura, Narashino; Tetsuo Kobayashi, Kobe, all of Japan

[73] Assignee: Rikagaku Kenkyusho, Saitama, Japan

[21] Appl. No.: 504,694

[22] Filed: Apr. 4, 1990

Related U.S. Application Data

[63] Continuation of Ser. No. 46,253, May 5, 1987, abandoned.

[30] Foreign Application Priority Data

May 9, 1986 [JP] Japan .................. 61-106393

[51] Int. Cl.$^5$ .............. C12N 11/00; C12N 11/02; C12N 11/08; C12N 11/14
[52] U.S. Cl. .................. 435/174; 435/176; 435/177; 435/180; 435/240.1; 435/240.2; 435/240.21; 435/240.23; 435/240.24; 435/252.1; 435/254; 435/822; 435/911; 435/918
[58] Field of Search ............. 435/174, 176, 177, 180, 435/240.1, 240.2, 240.21, 240.23, 240.24, 240.25, 243, 918, 822, 252.1, 254, 911

[56] References Cited

U.S. PATENT DOCUMENTS

| | | | |
|---|---|---|---|
| 2,146,326 | 2/1939 | Bergius et al. | 435/313 |
| 3,013,950 | 9/1959 | Gavin | 435/316 |
| 3,754,993 | 8/1973 | Oguchi et al. | 435/313 |
| 3,829,478 | 8/1974 | Ohorodnit et al. | 435/313 |
| 4,218,538 | 8/1980 | Church | 435/101 |
| 4,337,315 | 6/1982 | Fukushima et al. | 435/313 |
| 4,545,909 | 10/1985 | Atkinson et al. | 435/313 |
| 4,649,117 | 3/1987 | Familletti | 435/313 |
| 4,675,113 | 6/1987 | Graves et al. | |
| 4,863,856 | 9/1989 | Dean et al. | 435/240.25 |

FOREIGN PATENT DOCUMENTS 0197299 3/1985 European Pat. Off. .

OTHER PUBLICATIONS

Chemical Abstracts, vol. 83, No. 15, Oct. 13, 1985, p. 376.
Biotechnology & Bioengineering, vol. 26, No. 9, Sep. 1984, pp. 1098-1107 "A Continuous, Farm-Scale, Solid-Phase Fermentation Process for Fuel Ethanol and Protein Feed Production from Fodder Beets."
Manual of Industrial Microbiology and Biotechnology, American Society for Microbiology, Washington, D.C. 1986 pp. 66-83.
Fynn et. al, "Colonisation of polyurethane reticulated foam Biomass support by methanogen species" Biotechnology letters, v. 4 (9) 577-582, 1982.
Leighton, "Collagen-coated Cellulose Sponge", in Tissue Culture, Knise et al, ed., pp. 367-371, 1973.
Huysman et al, "Factors affecting the colonization of nonporous and porous packing materials in model upflow methane reactors", Biotech. Lett. v. 5(9), 643-648, 1983.
Poels et al, "High rate anaerabic digestion of piggery manure with polyurethane sponges as support material", Biotech. Lett. v. 6(11) 747-752, 1984.
van Wezel in Tissue Culture eds. Kruse et al 1973, pp. 372-376. "Microcarrier Cultures of Animal Cells", Academic Press. N.Y.
Rehm et al. Eds., Biotechnology, vol. 2, "Fundamentals of Biochemical Engineering", (Deerfield Beach, Fla. VCH, 1985) pp. 447-509.
Oda, Continuous Alcohol Fermentation Technologies Using Immobilized Yeast Cells pp. 597-609.

Primary Examiner—Y. Christina Chan
Attorney, Agent, or Firm—Brumbaugh, Graves, Donohue & Raymond

[57] ABSTRACT

A cell culture method proliferates microorganisms, particularly fungi such as molds, actinomycetes, animal cells, plant cells and so on to produce useful substances such as antibiotics, enzymes, proteins, polysaccharides, physiological active substances, and animal and plant hormones. Porous material including medium and cells to be proliferated is moved, whereby air is supplied to the surface of the porous material.

5 Claims, 4 Drawing Sheets

CELL CULTURE METHOD

This application is a continuation of application Ser. No. 07/046,253, filed on May 5, 1987, now abandoned.

FIELD OF THE INVENTION

This invention relates to a cell culture method of proliferating microorganisms, particularly fungi such as molds, actinomycetes, animal cells, plant cells and so on to produce useful substances such as antibiotics, enzymes, proteins, polysaccharides, physiological active substances, and animal and plant hormones.

DESCRIPTION OF THE PRIOR ART

In culture of fungi, a submerged culture method or a solid-state culture method is selectively used, depending on the kind of cells and the objective product. In the submerged culture method, pellet growth or pulpy growth occurs, depending on the kind of cells and culture condition. In the solid-state culture method, a natural substance such as rice or bran is used as medium, and culture is carried out in standing state. Recently, instead of the solid-state culture method in which a natural substance is used as a medium, a method in which a liquid medium is impregnated into spongy-like substance and culture is carried out in a standing state has been reported.

In culture of animal and plant cells, the submerged culture method and the solid-state culture method are also used. In the submerged culture method, a cell suspended culture method in which cells are directly suspended in the liquid medium, and another cell suspended culture method in which cells are encapsulated with or attached to carriers such as microcapsules or high-polymer resin pieces and suspended with the carriers are used. In the solid-state culture method, a method of attaching cells to the surface of a medium such as an agar medium and cultivating them in standing state is used.

As described above, in culture of fungi, the submerged culture method and the solid-state culture method have been conventionally used. The submerged culture method causes distinct problems, depending on the morphology of cellular growth as follows. In the pellet growth, according as the diameter of pellets becomes large, mass transfer of oxygen and nutritive substances becomes rate-controlling step. As a result, the cell growth rate decreases extremely and productivity of metabolites decreases. On the other hand, in the pulpy growth, the viscosity of the culture medium increases extremely, the medium is not mixed uniformly, and very high agitation power is needed. Furthermore, separation of the objective product from the medium including cells becomes difficult.

In the solid-state culture method, since the composition of solid natural medium varies in each lot, the amount of cellular growth and the yield of objective product varies greatly. And further since the objective product is stored in the solid medium, the separation of the objective product and its purification are difficult.

In the standing culture method of impregnating spongy material with liquid medium, since the objective product is stored in the liquid media, separation and purification of the objective product are easy. However, since contact of the medium with air is not sufficient and mass transfer is mainly caused by diffusion, cells grow nonuniformly in spongy material and growth rate decreases, consequently, the productivity of the objective product is suppressed.

The same problems as in the case of microorganisms such as fungi also arise in culture of animal and plant cells.

SUMMARY OF THE INVENTION

The above described problems are solved by this cell culture method having a step of moving a porous material including liquid medium and the cells to be proliferated, thereby supplying air to the surface of the porous material. According to this method, the contact of cells with liquid medium and air (oxygen) becomes easy, a uniform biological film is formed on the surface of the porous material, the cell growth rate increases, enzyme intracellular activity is enhanced, extracellular secretion is accelerated, and productivity of the objective product increases.

As the porous material may be used a formed synthetic high polymer such as urethane foam, natural sponge, or synthetic or natural fiber finished in one, two or three dimensions, in other words, finished to be filamentous, lace-like, fabric-like or plush.

With regard to the shape of the porous material, a sphere is preferable in view of its large ratio of surface to volume. However, a cube, rectangular parallelopiped or any other shape may be used so far as it does not obstruct the movement of the porous material.

The moving of the porous material may be made by shaking, vibration, mixing or a combination of these, in other words, up and down motion, to and fro motion, rotary motion, or a motion combining these may be used. The effect of this invention is enhanced if the porous material is constantly moved.

The amount of the liquid medium with which the porous material is impregnated is preferably 15 cm$^3$ to 60 cm$^3$ per 100 cm$^3$ of porous material. However, the amount varies, depending on the characteristics of the porous material such as its specific gravity and porosity, growth rate of used cells, production rate of the objective product and so on. If the impregnation ratio is increased so that the liquid medium covers the whole surface of the porous material, mass transfer of oxygen to the cells is prevented. On the other hand, if the impregnation ratio is extremely low, supply of the liquid medium to the cells becomes insufficient and nonuniform, and it becomes difficult to recover the objective product.

In this invention, since the mass transfer is not rate-controlling step, cellular growth rate and intracellular activity of enzymes increase, extracellular secretion is enhanced, and the productivity of a useful objective product such as an antibiotic (streptomycin, cephamycin, oxytetracycline, erythromycin, kanamycin, etc.), enzyme (amylase, protease, pectinase, cellulase, lipase, glucoamylase, glucoisomerase, etc.), protein (single cell protein, etc.), polysaccharide (arabinose, mannose, rhamnose, dextran, etc.), physiological active substance (vitamin $B_{12}$, vitamin $B_2$, vitamin C, etc.), or animal or plant hormone (auxin, cytokinin, gibberellin, steroid hormone, insulin, lymphokine, etc.) is enhanced, and mass production and direct recovery of highly concentrated objective product from culture solution becomes possible.

Hereinbelow, these and other effects will be described in detail by way of examples.

EXAMPLE

Example 1

Effect of moving porous material

Figure 1:
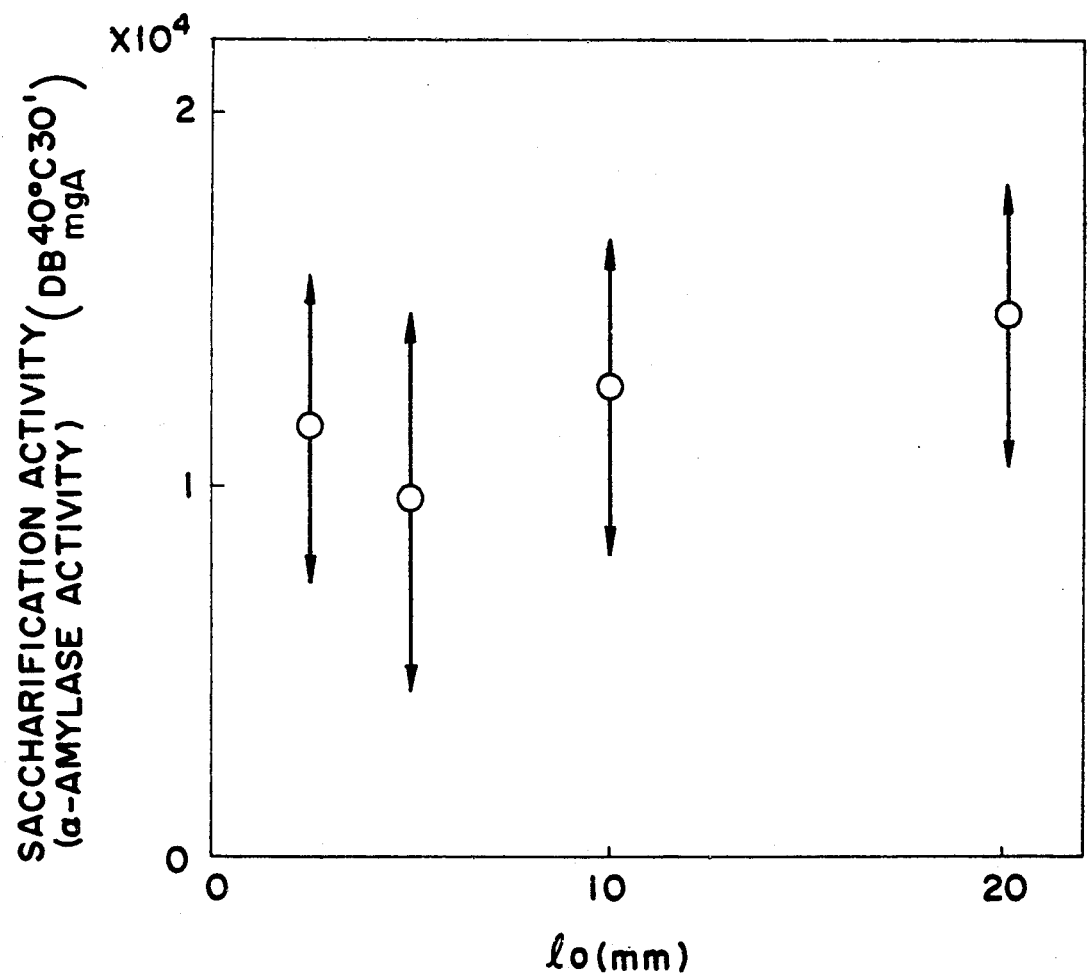
FIG. 1 is a graph showing the saccharification activity of JMC2058 strain to porous material size.

Pieces of cubic porous material about 5 mm in side length of urethane foam, 2.5 g in total weight (51.5 cm³ in total volume) were put into a conical flask. The porous material was impregnated with 30 ml Czapek medium consisting of 30 g saccharose, 5 g yeast extract, 1 g $K_2HPO_4$, 3 g $NaNO_3$, 0.5 g $MgSO_4.7H_2O$, 0.5 g KCl, and 0.01 g $FeSO_4.7H_2O$, with one liter distilled water. Next, Aspergillus oryzae (JCM2239) was inoculated into the flask. Culture was carried out in two ways: by standing culture in an incubator at 24° C. and by shaking culture at 200 rpm shaking rotational speed at 24° C.

At the sixth day from the beginning of the culture, the urethane foam was taken out, the liquid medium was wrung out and saccharification activity (α-amylase activity) of the liquid medium was measured by the Blue-Value method. The same experiment was carried out for Aspergillus oryzae var. brunneus(JCM2058). The results are shown in Table 1.

TABLE 1

| Saccharification activity (α-amylase activity) | | |
|---|---|---|
| Culture method | JCM2239 | JCM2058 |
| Standing culture | 570 | 5465 |
| Shaking culture | 2230 | 7038 | wherein α-amylase activities are shown in ($DB_{mg}A^{40°C.}_{30'}$), which is the amount of amylose in milligram units separated in 30 minutes at 40° C.

For both kinds of cells, saccharification activities in the shaking culture of cells were larger than those in the standing culture. In the standing culture, pieces of porous material were combined with each other by mycelium, growth of cells on the surface of the porous material was not uniform, and medium and oxygen did not contact the cells well. On the other hand, when the porous material was moved by shaking, oxygen and medium contacted the cells well, and the biological film was uniformly formed on the whole surface of the porous material.

Example 2

Effects of size of porous material and impregnation ratio of liquid medium.

Pieces of cubic porous material of urethane foam 2.5 g in total weight (51.5 cm in total volume) of side lengths about 20 mm, 10 mm, 5 mm and 2.5 mm were put into respective 500 ml flasks. The same Czapek medium as in Example 1 was poured in amount of 46 ml, 31 ml, 15 ml, 10 ml, 8 ml and 2.5 ml into the respective flasks to prepare 90%, 60%, 30%, 20%, 15% and 5% impregnation ratios for each size. Next, Aspergillus oryzae var. brunneus(JCM2058) was inoculated into the flasks. Shaking culture was carried out at 200 rpm shaking rotational speed at 24° C. At the sixth day from the beginning of the culture, the urethane foam was taken out and the liquid medium was wrung out and saccharification activities were measured The results are shown in Table 2.

TABLE 2

| Saccharification activity (α-amylase activity) of JCM2058 | | | | | | |
|---|---|---|---|---|---|---|
| Size | Impregnation ratio | | | | | |
| (length) | 90% | 60% | 30% | 20% | 15% | 5% |
| 20 mm | 11259 | 13136 | 19502 | 21294 | 21841 | 6230 |
| 10 mm | 12640 | 7407 | 13827 | 25441 | 22394 | 7146 |
| 5 mm | 3628 | 7038 | 9172 | 14730 | 15399 | 4462 |
| 2.5 mm | 6427 | 8721 | 10535 | 18413 | 19398 | 2603 |

Figure 2:
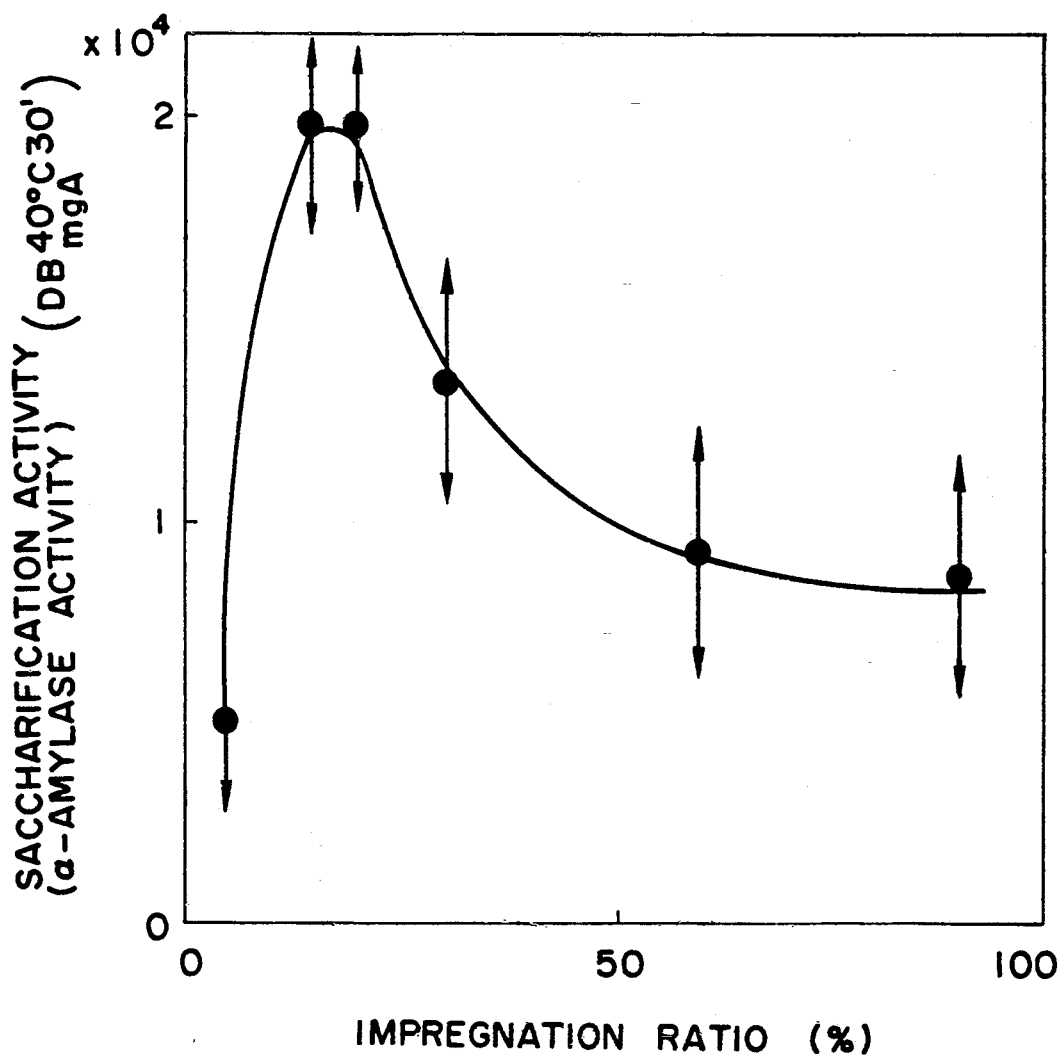
FIG. 2 is a graph showing the saccharification activity of JMC2058 strain to impregnation ratio of liquid medium.

FIG. 1 shows the effect of porous material size on saccharification activity and FIG. 2 shows the effect of liquid medium impregnation ratio on saccharification activity.

In this example, no effect of porous material size on saccharification activity was observed. With regard to the impregnation ratio, a smaller ratio tends to increase the saccharification activity. However, too small a ratio slightly reduces the activity. This may be because when the impregnation ratio is too small, supply of medium to the biological film is not sufficient and growth of cells is not uniform in porous material. It can be found from FIG. 2 that from the point of yield an impregnation ratio of less than 60% preferable while from the the point of easy recovery of the objective product an impregnation ratio of more than 15% is preferable.

Example 3

Effect of rotary mixing of porous material by use of rotary drum

Pieces of cubic porous material of urethane foam about 10 mm in side length, 120 g in total weight (3500 cm³) were put into a rotary drum 25 cm in diameter and 35cm in depth. As in Example 1, the porous material was impregnated with 1000 ml Czapek medium. Aspergillus oryzae var. brunneus(JCM2085) was inoculated, and culture was carried out at 24° C., 60 rpm rotational speed, and 0.5 l/min air flow. At the sixth day from the beginning of the culture, the urethane foam was taken out, the liquid medium was wrung, and the saccharification activity (α-amylase activity) was measured.

Two controls were prepared to be compared with the example. The same pieces of urethane foam 2.3 g in weight (48 cm³ in volume) were put into 300 ml conical flasks, respectively. In the control 1, the urethane foam was impregnated with 30 ml Czapek medium. Culture was carried out by the standing culture method at 24° C. In the control 2, 100 ml Czapek medium was poured into the 300 ml conical flask. Culture was carried out by the shaking culture method at 24° C. and a shaking rotational speed of 200 rpm. Saccharification activities for controls 1 and 2 at the sixth day from the beginning of the culture were measured. The results are shown in Table 3.

TABLE 3

| Saccharification activity (α-amylase activity) of JCM2058 | |
|---|---|
| Culture method | Saccharification activity |
| rotary drum type culture | 12116 |
| standing culture (control 1) | 5465 |

TABLE 3-continued

| Saccharification activity (α-amylase activity) of JCM2058 | |
|---|---|
| Culture method | Saccharification activity |
| submerged culture (control 2) | 4403 |

In the standing culture method (control 1), as in example 1, growth of cells was not uniform. In the submerged culture method (control 2), cells grew in pulpy-like, but pellets about 5 mm in diameter were included in the liquid medium, and the viscosity of the liquid medium was high during culture. On the other hand, in the culture method using a rotary drum, the pieces of porous material were rotated and mixed, so they did not always contact each other, and a uniform biological film of cells was formed. As shown in Table 3, the saccharification activity (α-amylase activity) in Example 3 was two or three times as large as those in the standing culture method and the submerged culture method.

Figure 3:
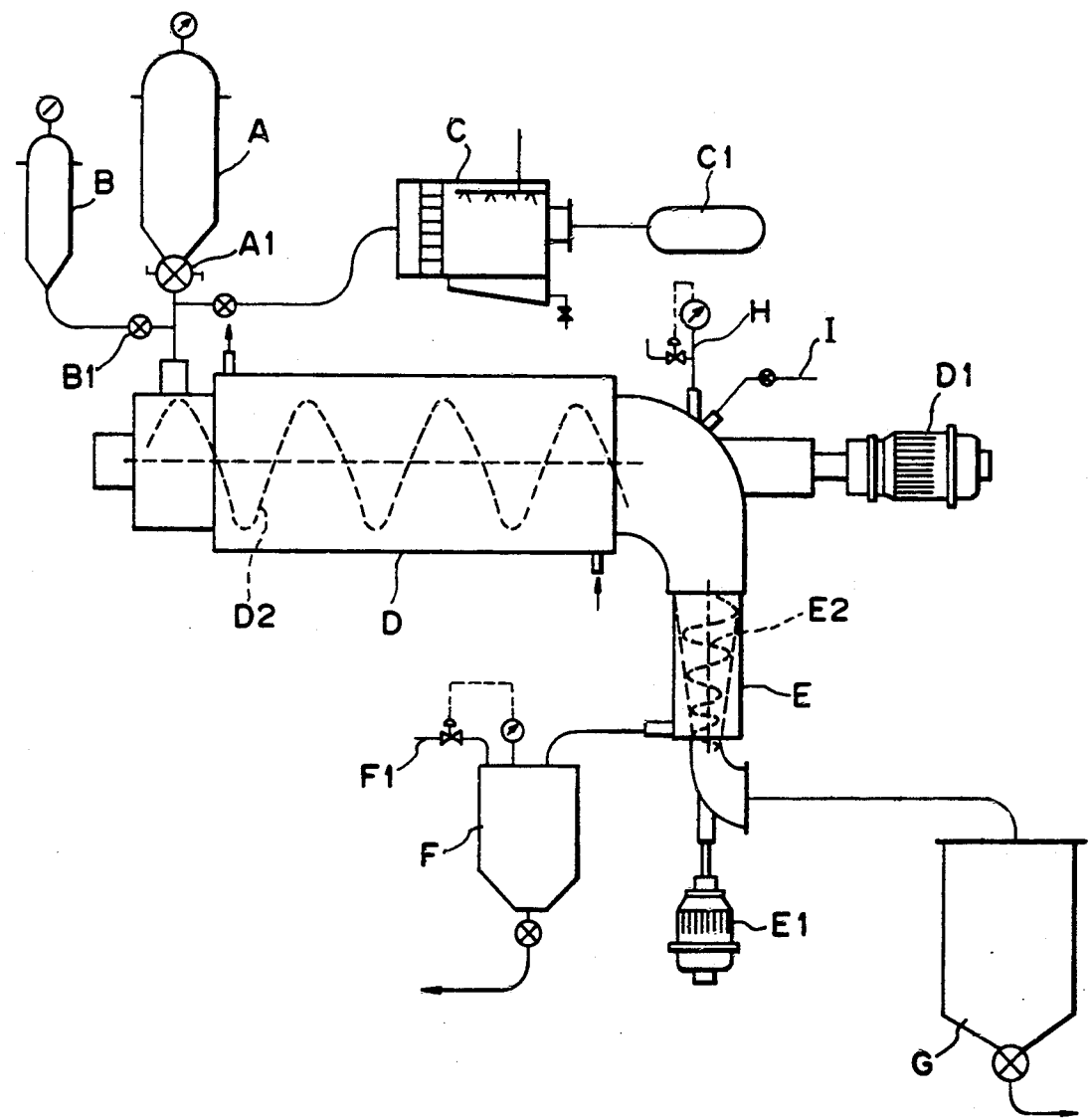
FIG. 3 is a shematic diagram of a cell culture system for carrying out this invention in industrial level.
Figure 4:
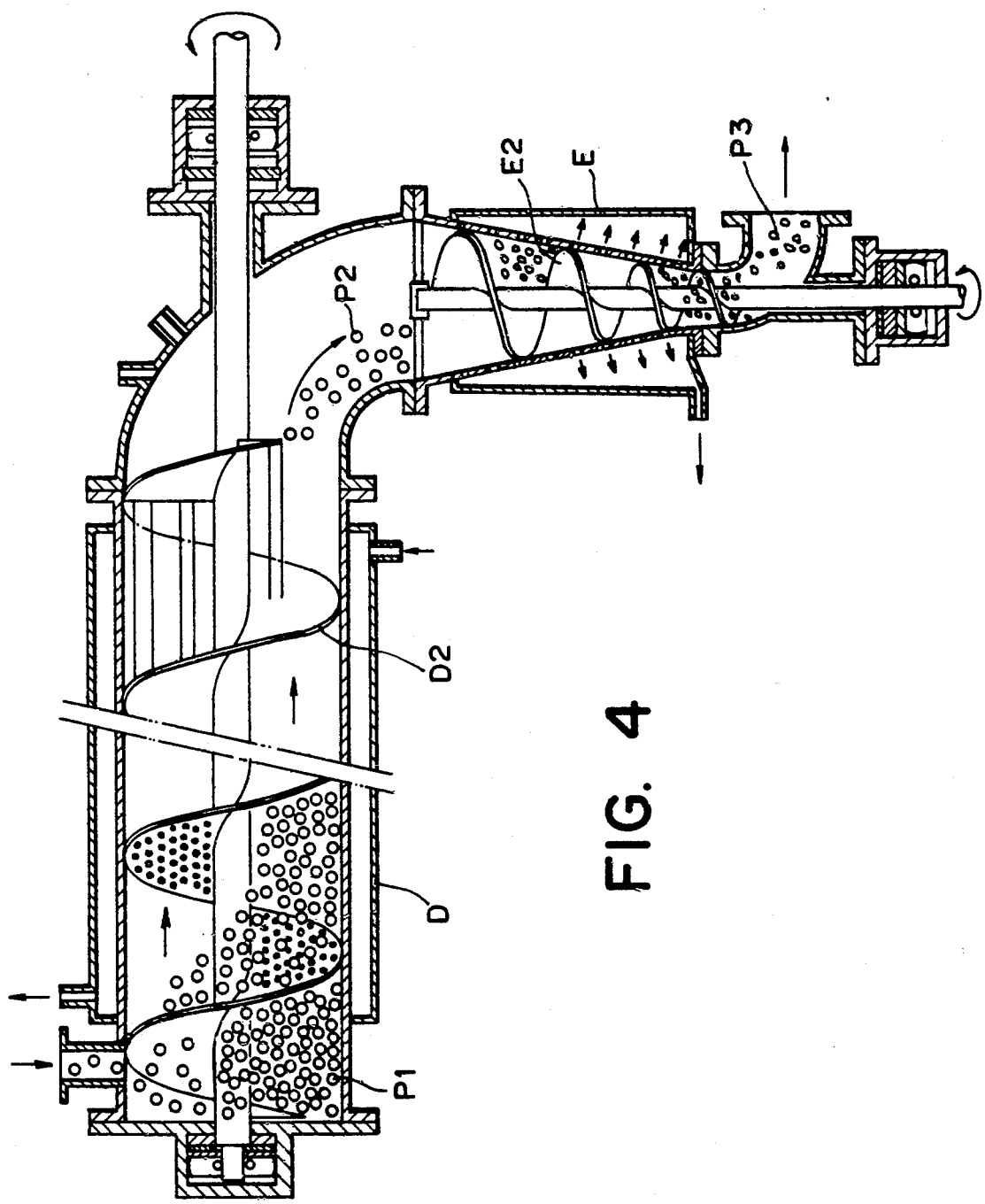
FIG. 4 is a detail sectional view of a cell culture apparatus and a conical shape press used in the cell culture system of FIG. 3.

Referring to FIGS. 3 and 4, there is shown a cell culture system for carrying out this invention in industrial level. A predetermined amount of porous material including liquid medium aseptically is supplied continually or in batchwise from a porous material supply tank A through a rotary supply valve A1 into a cell culture apparatus body D. Cells are simultaneously supplied from a cell supply tank B through a supply valve B1 into the cell culture apparatus body D, and the supplied cells are inoculated on the porous material. Temperature and moisture controlled and pressurized air is continually supplied from a fan C1 through an air-conditioner C. The pieces of porous material P1 including the cells and liquid medium are kneaded and mixed by a screw kneader blade D2 which is driven by a variable speed electric motor D1, and cell culture is accelerated. After proliferation of cells or production of an objective product finishes, the pieces of porous material P2 are pressed in a conical shape press E by a screw press blade E2 which is driven by a variable speed electric motor E1, and the liquid medium are separated from cells. The separated liquid medium and the liquid removed and cell including porous material P3 are recovered in a liquid medium recover tank F and a porous material recover tank G, respectively. A pressure control exhaust nozzle H having a pressure control valve is disposed on an outlet of the cell culture apparatus body D, and another pressure control exhaust nozzle F1 is disposed on the conical style press E, whereby pressures in the cell culture apparatus body D and the conical style press E are maintained higher than that out of those apparatus. In the case that the objective product is an intracellular product, sterile cleaning fluid is injected by a sterile cleaning fluid supply pipe I, cells are cleaned and recovered in the porous material recover tank G together with the porous material after the porous material are pressed and dehydrated.

What is claimed is:

1. A cell culture method comprising the steps of:
  (a) impregnating a plurality of pieces of porous material with a liquid nutrient medium, said liquid medium being impregnated in an amount of from 15 cm$^3$ to 60 cm$^3$ per 100 cm$^3$ of porous material;
  (b) inoculating cells of fungi or Actinomycetes on the impregnated porous material; and
  (c) incubating the inoculated porous material without adding additional medium, wherein the pieces of porous material are agitated relative to one another during incubation such that air supply to the surface of the pieces of porous material is maintained.

2. A cell culture method comprising the steps of:
  (a) impregnating a plurality of pieces of porous material with a liquid nutrient medium;
  (b) inoculating cells of fungi or Actinomycetes on the impregnated porous material; and
  (c) incubating the inoculated porous material while moving the pieces of porous material relative to one another during growth of the cells such that air supply to the surface of the pieces of porous material is maintained, wherein the amount of liquid medium present during incubation is not so low as to be insufficient to allow growth of the inoculated cells, and not so high as to cover the whole surface of the porous material and retard mass transfer of oxygen to the cells.

3. The cell culture method of claim 1, wherein the agitation of the porous material is conducted by shaking, vibration, mixing or a combination of these.

4. A cell culture method according to claim 1, wherein the cells are fungi.

5. A cell culture method according to claim 1, wherein the cells are Actinomycetes.

* * * * *